United States Patent [19]

Stecher et al.

[11] 4,410,872
[45] Oct. 18, 1983

[54] ELECTRICAL THICK-FILM, FREE-STANDING, SELF-SUPPORTING STRUCTURE, AND METHOD OF ITS MANUFACTURE, PARTICULARLY FOR SENSORS USED WITH INTERNAL COMBUSTION ENGINES

[75] Inventors: Günther Stecher, Ludwigsburg; Herbert Zimmermann, Freiberg, both of Fed. Rep. of Germany

[73] Assignee: Robert Bosch GmbH, Stuttgart, Fed. Rep. of Germany

[21] Appl. No.: 181,892

[22] Filed: Aug. 27, 1980

[30] Foreign Application Priority Data

Apr. 22, 1980 [DE] Fed. Rep. of Germany ....... 3015356

[51] Int. Cl.$^3$ ............................................. H01C 10/10
[52] U.S. Cl. .................................... 338/114; 361/283
[58] Field of Search ................... 338/114, 69; 361/283

[56] References Cited

U.S. PATENT DOCUMENTS

| | | | |
|---|---|---|---|
| 3,328,653 | 6/1967 | Wolf, Jr. ............................. | 361/283 |
| 3,626,350 | 12/1971 | Suzuki et al. ....................... | 338/69 |
| 4,084,438 | 4/1978 | Lee et al. ........................ | 361/283 X |
| 4,151,578 | 4/1979 | Bell ..................................... | 361/283 |
| 4,184,189 | 1/1980 | Davis et al. ......................... | 361/283 |
| 4,257,305 | 3/1981 | Friend et al. ......................... | 338/69 |
| 4,268,815 | 5/1981 | Eventoff et al. ................ | 338/114 X |
| 4,314,227 | 2/1982 | Eventoff .............................. | 338/69 |

*Primary Examiner*—C. L. Albritton

*Attorney, Agent, or Firm*—Frishauf, Holtz, Goodman & Woodward

[57] ABSTRACT

A free-standing, self-supporting layer of glass-ceramic or crystallized glass is applied by thick-film technology over a presintered layer made of a vaporizable or etchable material which, after sintering the thick-film glass-ceramic or crystallized glass layer (3) to a substrate (1), is removed by heating or etching. The layer (2) to be removed is preferably applied in paste form with the glass-ceramic thick-film layer (3) thereover either in form of a crossing bridge, as a partially covering cantilever, or entirely surrounding the layer 2, in which latter case the thick-vaporizable film layer (3) is of porous construction so that the volatile or components of the underlying layer (2) can escape through the thick-film layer (3). A typical layer which is volatile or vaporizable includes carbon black, a resin binder and a solvent, applied to a substrate, for example of ceramic or enameled metal, over which the glass-ceramic layer is applied. Electrically conductive tracks can be applied directly on the substrate beneath the layer (2) to be removed, and to the thick-film layer, or in the form of strain or temperature-sensitive resistors, for connection to an external circuit evaluating deformation of the free-standing layer by capacitative or resistance change, to obtain pressure sensors, vibration sensors, acceleration sensors, and the like, of minute construction. A typical dimension of the thick-film layer is in the order of tens of micrometers, with the free space after removal of the filler (2) being also about in the order of tens of micrometers.

6 Claims, 6 Drawing Figures

ELECTRICAL THICK-FILM, FREE-STANDING, SELF-SUPPORTING STRUCTURE, AND METHOD OF ITS MANUFACTURE, PARTICULARLY FOR SENSORS USED WITH INTERNAL COMBUSTION ENGINES

REFERENCE TO RELATED APPLICATION:

U.S. Ser. No. 181,839, filed Aug. 27, 1980, by STECHER, SPITZENBERGER and MULLER, "Pressure Sensor", the disclosure of which is hereby incoprorated by reference.

The present invention relates to electrical thick-film, free-standing, self-supporting structures, and methods of their manufacture, particularly adapted for sensor structures to sense operating or control parameters of internal combustion engines. The sensors and the method of their manufacture have utility independently of the engine with which they may be associated and, for example, can also be utilized to sense pressures, temperatures, or gas flow, and provide, in combination with suitable electrical circuitry, electrical output signals representative of the particular parameter. The structure and the method are also applicable in the manufacture of gas composition sensors, for example, in which gas flow to a particular structural zone of selected material has to be made possible or to be controlled.

BACKGROUND AND PRIOR ART

Thick-film circuits are well known in which pastes of an active material comprising metal powders, glass, glass ceramic powders or mixtures of glass and metal oxides are applied on ceramic substrate, usually in plate form. The pastes can be applied by printing, preferably on a ceramic substrate. After application of the paste, they are fired at a temperature of about 850° C. in an oxidizing atmosphere and then appropriate layers will result which, in dependence on the pastes which we used, may be metallic, glass, glass ceramic, or electrical resistance-type layers. These layers, upon firing, combine with or bond entirely with the surface of the substrate upon being fired, to then form a securely adhering structure therewith. It is also known to superpose layers made in this manner by repeating the method just described utilizing, alternatingly, metallic or insulating layers, so that sandwiches of superposed metallic and insulating layers will be obtained. Upon firing, the respective layers bond securely to each other.

THE INVENTION

It is an object to provide free-standing, self-supporting structures which are not continuously bonded to or adhered on a substrate, utilizing thick-film technology, for example to form hollow structures, free-standing tongues, or the like.

Briefly, the area of the substrate over which the thick-film layer is to be applied first has a filler material which can be later removed applied thereto. The filler material preferably has a substance which will gasify upon being exposed to high temperature. A thick-film paste is applied over the filler, preferably by printing, having an active component which is a glass or glass ceramic, or a crystallizing glass, well known as such in thick-film technology. This layer entirely or partially covers the filler and is adhered, at least in part, on the substrate. In a first firing process, the thick film layer is solidified. This first firing process, preferably, is carried out in a protective gas, for example in a nitrogen atmosphere. In a subsequent firing process, preferably in an oxidizing atmosphere, the filler is removed, e.g. gasified or combusted. If the thick-film layer is porous, a complete hollow membrane can be made by permitting the combustion gases of the filler to escape through the porous structure of the thick-film layer thereover. A metal coating can be applied over the thick-film layer which can form a plate of a capacitor; or the metal may be in form of strips, for example in order to connect applied thick-film resistors, for use in a bridge circuit; or temperature-sensitive material can be applied.

In accordance with an embodiment of the invention, the filler material comprises a substance which can be removed by etching, for example copper, and removal of the substance, rather than by gasifying, or combusting the filler will be carried out by etching the filler away.

In accordance with a feature of the invention, the structure will be a free-standing, for example hollow, self-supporting, thick-film which is adhered in part to a substrate, and in part forms a hollow space with the substrate, or a free overlapping projecting tongue.

DRAWINGS

Figure 1:
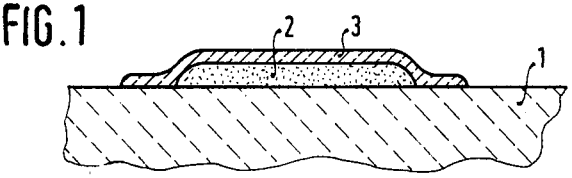
FIG. 1 is a highly schematic cross-sectional view of a finished structure in accordance with the invention, which will also be used in connection with the explanation of the method of making the same.
Figure 2:
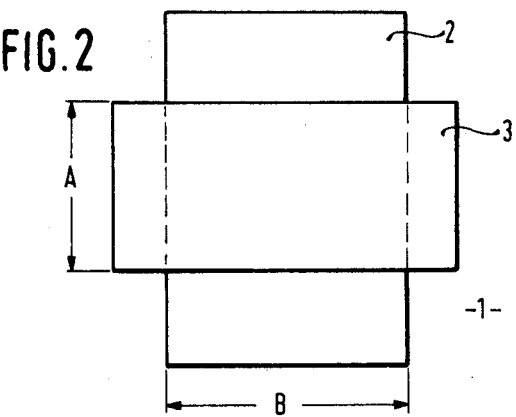
FIG. 2 is a schematic top view illustrating dimensional relationships.

Embodiment of FIGS. 1 and 2, and general description of method:

A substrate 1 which, for example, may be ceramic, glass, an enameled metal plate, or the like, has a filler material 2 applied thereto, for example by printing. A thick-film layer 3 is to be applied over the filler material to eventually be self-supporting, as shown for example by the hollow space or chamber 8 in FIG. 6.

The filler 2 and/or the portion of the thick-film top cover 3 which are applied to the substrate 1 can be applied directly, as shown in FIG. 1, on the substrate. They may, however, also be applied over already previously applied layers if the self-supporting structure has to be build up on top of these layers; or in order to increase the thickness of the respective layers. Thus, for example, the filler 2 can be applied in several application steps to reach the requisite thickness; and the thick-film layer 3 in several application steps thereover, so that it will have the appropriate thickness.

Filler 2, preferably, comprises primarily soot or carbon black which, together with a suitable resin dissolved in an appropriate organic solvent, forms a paste which can be applied by screen printing.

The so applied filler, for example by screen printing, is fired in a furnace under a protective gas atmosphere, for example and preferably nitrogen, and at such temperatures at which the filler 2 sinters to its final desired thickness over which the partially free-standing layer 3 should be applied after printing process thereof. The firing temperatures, depending on the material used of which the layer 3 is to be constituted, should be in the range of between 800° to 1000° C., but they may be in the range of between 400° to 600° C. By repeated printing and subsequent firing, the sintered filler 2 can be built up to have the desired thickness.

A thick-film layer is then applied over the filler 2 and the substrate 1. The thick-film layer, preferably, comprises a glass ceramic or a crystallizing glass. Suitable pastes for application, again by printing, can be sintered in a protective gas atmosphere, for example nitrogen, to a solid mass. This solid mass will bond with the substrate 1 except in the region where the filler 2 had previously been applied, or with an already previously applied layer of thickfilm material. The self-supporting structure can build up completely on top of that layer or such a material is applied only there, the layer 3 is adhered on.

A substantial number of commercially available pastes provide solid structures and masses which are free of carbon residue only if they are fired in an oxidizing atmosphere. Such pastes can be used as base material for the layer 3 if, during heating of the substrate to about 500° C. in a protective gas atmosphere of the furnace, a predetermined oxygen content is provided, for example about 800 ppm, and an increased speed of flow of the furnace atmosphere counter the movement of the support or transport belt which transports the substrate through the furnace is generated. The result will be that the organic components of the pastes for layer 3 will gasify, the sintered filler 2, however, will not yet incinerate.

A further firing step then is carried out which, in contrast to the previously described steps, is done in an oxidizing atmosphere. In this step, the filler 2 is combusted without residue, resulting in an at least partially free-standing, self-supporting layer 3—see FIG. 6.

The thickness of the range of the layers 3 over the filler 2 at the first firing process need not be thick, for example in the order of about 0.03 mm, and the layer can be of a glass ceramic material of suitable porosity. With these conditions, the filler 2 will completely incinerate even in a space which is entirely covered by the cover layer 3 since the combusting gases can escape through the layer 3 which is porous.

Figure 5:
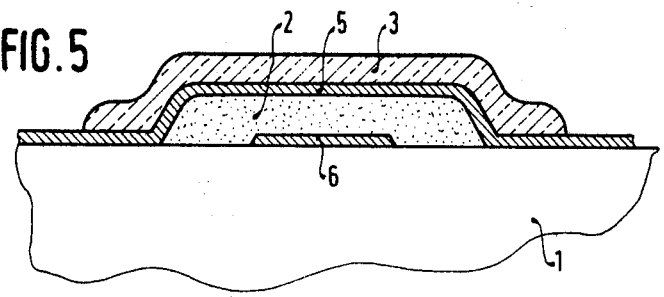
FIG. 5 is a highly schematic cross section through a capacitative pressure sensor prior to removal of the filler, and illustrating a starting step in the manufacture.

In accordance with a feature of the invention, the free-standing layer may carry a suitable metallic or resistance layer 5—see FIG. 5—at its underside, which is bonded tightly to the glass ceramic layer 3. The layer 5 onto filler 2 can be made in a preceding application step of the metallic layer and a separate firing step; alternatively, it can be fired together with the glass ceramic layer 3. If the layer 5 is to be a resistance layer, rather than a highly conductive one, it is preferably always made in a separate firing step prior to firing of the layer 3, and will then bond with the glass ceramic layer when the glass ceramic layer 3 is being fired.

FIG. 2 is a top view of the embodiment of FIG. 1, and illustrates dimensional relationships. The width A of the cover layer 3 and the width B may be of the same order of magnitude, so that the cover layer 3 will form a bridge structure.

The dimensional relationships are not critical; for example, the width A of the cover layer 3 may be substantially wider, for example 100 times the width B of the filler 2. The result will be a tunnel-shaped duct. This embodiment is particularly suitable if combustion of the filler 2 is carried out by permitting the combustion residues to escape through the cover layer 3 which is porous. The height H (FIG. 1) of the resulting tunnel can then be very small with respect to its length. For example, the height H may be 0.01 mm, whereas the length A may be several cm long. The tunnel need not be a straight line; it can be of undulating shape, and can include branches, or be in form of a labyrinth.

Figure 3:
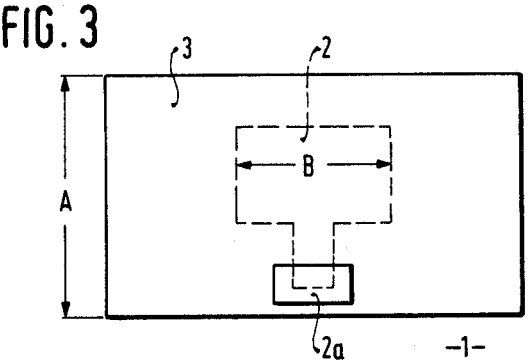
FIG. 3 is a top view of another embodiment, also illustrating dimensional relationships.

Embodiment of FIG. 3: The cover material of the layer 3 surrounds the filler 2 in all directions. The shape of the filler and the shape of the cover material, can be as desired, and the rectangular configuration shown in FIG. 3 is merely one example. For example, the filler 2 could also be circular. After firing, and escape of the filler 2 through the pores of the layer 3, an entirely closed space is provided. If the filler 2 has a lateral extension 2', which is left uncovered by material 3 in the region 2a, for example by being masked upon application of the thick-film layer 3, the space 2 will be externally accessible.

Figure 4:
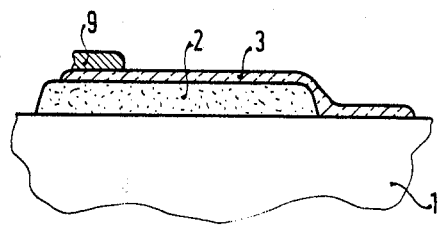
FIG. 4 is a fragmentary side view of another embodiment, prior to removal of the filler.

Embodiment of FIG. 4: The cover material of the layer 3 is bonded to the substrate 1 or to any layer applied thereto only on one side so that a free-standing tongue 43 will be formed after removal of the filler 2. The plan view of the tongue 43 can be in accordance with any desired configuration, for example in elongated strip form, that is, rectangular, part-circular, oval, or the like. For use as an acceleration sensor, the end portion of the tongue 43 can have a weight 9 applied thereto, as will appear below. The thickness of the layer 3 can be increased in one or sequential printing-firing steps. The materials of the layer 3 need not all be the same; other suitable glass ceramic materials or crystallizing glasses can be used than those which were utilized when the paste of the first layer 3 was applied. The layers forming the composite thick-film 3 may have electrical conductive tracks, resistors, or other electric layers applied thereto in accordance with well known processes of thick-film technology. These conductive tracks, resistors, or other electrical layers, if desired, can be electrically connected to other structures supported on the substrate 1. Gas-tight closing of hollow spaces 8—see FIG. 6—made in accordance with the process described, or of tunnels 2' and hollow spaces 2—see FIG. 3—can be obtained by applying an amorphous glass layer on and over the other structural or electrical components on the substrate 1, as desired. Such an amorphous glaze has been omitted from the drawings, for clarity, since its use and application are well known.

Application of the embodiments described, and extension of inventive concept:

Embodiment of FIGS. 1 and 2, bridge construction: Air insulation can be provided between crossing conductive tracks applied in thick-film technology instead of the previously customary separation by a glass-ceramic insulating layer. The glass-ceramic insulating layer, of course, is used in addition.

Figure 6:
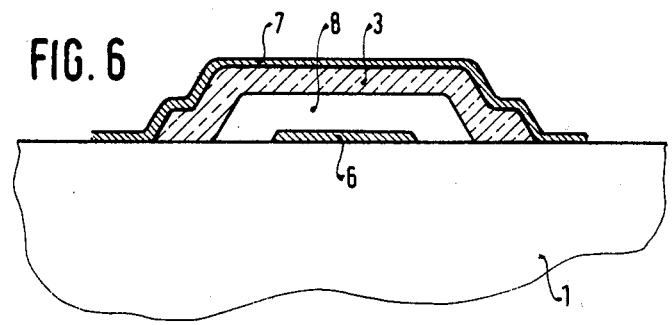
FIG. 6 is a view similar to FIG. 5, illustrating one form of a finished sensor.

FIG. 6 illustrates a lower conductive track 6 applied to the substrate 1. The space 8 above the conductive track 6 forms an air gap which is further separated from an upper conductive track 7 by the glass-ceramic layer 3.

The advantage of this arrangement is the decrease of parasitic capacity which is formed by the crossing of the track 6 and the track 7. The decrease is more than one order of magnitude. Corrosion between conductive tracks which may arise under voltage stress in operation, in the presence of comparatively high ambient humidity, additionally can be prevented.

The conductive tracks 6 can be applied to the substrate by any suitable manner as well known, for example by vapor deposition, printing and firing, adhesion, or the like. The filler 2 is then applied over the substrate 1 after the conductive track 6 has been applied, and is subsequently removed as previously described.

The bridge construction, with the space 8, can be used also to make a switch. FIG. 5 illustrates a conductive track 5 which is applied to the lower side of the thick-film layer 3. Upon removal of the filler 2, and depression of the conductive track 5 together with the thick-film layer 3, an electrical connection between tracks 5 and 6 can be obtained, so that the element will form a switch. Deformation of the outer composite layers 3, 5 by an external force is schematically indicated by the force arrow P which, after removal of the filter 2, can cause electrical connection between tracks 5 and 6.

The bridge construction as well as the free-standing construction of FIG. 4 can be used to form a fast-response temperature sensor. The layer 3 can be made very thin—a thickness of 0.02 mm is quite easily obtained—so that the heat capacity of the layer 3 is very small. Its response to temperature changes, and particularly its temperature rise when exposed to ambient high temperatures, is very high. Application of a temperature-sensitive resistor on the layer 3, then, suitably connected, for example in a bridge circuit, will result in a high response speed temperature sensor. Such a sensor is suitable for temperature sensing or monitoring of temperatures of gases, for example exhaust gases of an internal combustion engine, for instance an automotive-type internal combustion engine.

The bridge construction can also be used as an oscillating system to detect pressure variations, oscillations, or vibrations of a structure to which the substrate 1 is connected. When these pressure variations, vibrations, or oscillations reach the inherent frequency of the bridge, the bridge will oscillate with it, and resistors applied on the layer 3, for example by printing, and which change their resistance when being elongated or compressed, that is, subject to strain or compressive force, and suitably connected in an evaluation network, for example a bridge circuit, can be used to detect oscillations or vibrations at specific frequencies. In another form, conductive strips 5 (FIG. 5) or 7 (FIG. 6) in combination with a conductive track 6, can be connected in form of capacitors to a suitable evaluation circuit which evaluates change in capacity between the respective electrodes and hence permit evaluation of frequency of vibrations, as well as of static pressure P.

Application of the tunnel constructon —FIG. 3: This construction is used, for example, in connection with gas sensors in which a reference gas is to be applied, or in which application of a gas to a gas-sensitive solid electrolyte body has to be controlled. Such gas sensors are used, for example, as lambda-sensors to test the exhaust gases of internal combuston (IC) engines for oxygen content.

Gases are applied along the plate-like substrates by applying a reference gas, typically oxygen, from the air to a solid electrolyte oxygen ion conductive body.

The flow resistance of gases in narrow capillary ducts can also be utilized. Thus, the open duct 2' can be made so small that it can be used as a flow-constricting or controlling duct to control the diffusion of gas molecules to a lambda-sensor operating in the polarographic mode, that is, having a voltage applied thereacross and permitting flow of the diffusion limiting current in accordance with oxygen content of the gas applied. This, also, permits measuring of the oxygen content in gases.

The tunnel—application also permits construction of fluidic circuits in combination with thick-film circuits by applying electrodes which are suitably connected to evaluation circuits and evaluating parameters between the electrodes, for example resistance, capacity, and the like. The electrode constructions of FIGS. 5 and 6 may be used in this manner.

Application of closed spaces—FIG. 3: The space 8 (FIG. 6) which is left after removal of the filler 2 in the structure of FIG. 3 can be closed by, for example, sealing the window 2a. The result will be a closed hollow space which can be filled with a gas at a reference temperature, or can be evacuated, for example. The structure can then operate as a thick-film pressure sensor with an evacuated chamber, particularly when using electrodes, for example as illustrated in FIG. 6.

The structure can also be used as a temperature sensor without temperature-depending resistors by filling the hollow space 8 with a reference gas. The free-standing, self-supporting membrane 3 will then have strain sensing resistors applied thereto, for example in a bridge circuit, which change resistance upon being subjected to strain or compressive force, or two electrodes 6, 7, as in FIG. 6 or 6,5 as in FIG. 5, to form a capacitor which varies its capacity with deformation of the thick-film layer 3 and the electrode 7 in FIG. 6 or 5 in FIG. 5 thereon.

The construction also lends itself to making a pressure-sensitive switch, for example if constructed as in FIG. 5, in which the space 2, 2' is closed off. If the external pressure changes, for example rises above the internal pressure, the free-standing, self-supporting layer will be dropped to such an extent that an electrical connection will be effected between the conductive tracks 5 and 6 (see FIG. 5). The elements are sensitive and a very small increase of external pressure, that is, force P, over the pressure in the inside of the space 8 can make contact.

Cantilever construction, FIG. 4: the free-standing tongue or cantilever layer 3 of FIG. 4 can be used to build a strain gauge, to determine bending strains, pressure variations, or vibration of structural elements to which the substrate 1 is connected. The inherent frequency of oscillation of the system can be adjusted by controlling the length of the cantilever 3, for example by making the cantilever 3 to a maximum length and then cutting it to desired size by a laser beam. Extremely accurate control of the length of the tongue 3 which is left can thus be obtained. The elastic deformation of the tongue 3 can be sensed by transducing it to an electrical signal by printing an electrical resistance layer on the tongue 3, or utilizing a capacity effect by applying electrodes similar to electrodes 5 or 7 (FIGS. 5, 6) and an additional electrode 6 (FIGS. 5, 6).

This structure is, preferably, used as a detonation or "ping" or "knock" sensor in IC engines, particularly of the automotive type. The ordinary knocking frequencies are in the order of about 10 kHz. A cantilever tongue 3 which is to be tuned to approximately such a frequency must have a length of about 2 mm, which can be readily made.

The apparatus of FIG. 4 can also be used as an acceleration sensor. For such use, a swinging mass 9 applied to the free cantilever end of the tongue 3 is preferably used. This mass 9 can be applied by printing-on of gold, or by coating a conductive track applied at the end portion of the tongue 3 with a lead solder to provide a weighted end to the tongue 3. Elastic deformation can be transduced into an electrical signal either by applying thick-film resistors, for example by printing, on the tongue 3 or, again, by utilizing capacitive effects, as explained in connection with FIGS. 5 and 6. This type of acceleration sensor can be used, for example, as a sensor to trigger inflation of passenger restraint air bags in automotive vehicles, that is, to sense impacts while being essentially immune to decelerations arising in ordinary traffic conditions.

The composition of the filler 2, in a preferred form, is such that it will vaporize or become volatile and will dissipate under heat. The concept of the invention may, however, be used wherein the filler is made of a metal or metal-containing paste, and preferably copper which can be applied by printing, over which the layer 3 is then applied as above described. To then form the layer 3 in self-supporting position, as shown in FIG. 6 after removal of the filler, the filler metal or the metal paste is removed by etching.

Various changes and modifications may be made, and features described in connection with any one of the embodiments may be used with any of the others, within the scope of the inventive concept.

A paste suitable for removal by heat for the filler 2, for example, has the following composition:
primary filler: carbon black,
resin: Polyesterresin of isophthalic acid
solvent: Terpineol, Styrol
The foregoing being mixed into a paste in these proportions: carbon/resin/solvent/additive
10/40/40/10% weight
presintering temperature for the above to obtain desired thickness: 700° C.
composition of layer 3 applied thereover:
solid material: $PbO/B_2O_3/SiO_2$-Glass
filler substance: $Al_2O_3$
presintering temperature to remove binder or solvent: 125° C. (solvent), 300°–500° C. (Binder)
sintering temperature under reducing atmosphere condition: 950° C.
approximate thickness of layer 2 or 3 per application of layer: 0,02 mm (layer 2), 0,02 to 0,04 mm (layer 3)
approximate range of final thicknesses of filler layers 2 with multiple layers, suitable for construction of bridge of FIGS. 1, 2, hollow space of FIG. 3 or cantilever of FIG. 4: 0,02 mm to 0,1 mm
approximate range of thickness of layer 3: 0,02 to 0,1 mm
suitable metals for tracks 6, 7: PdAg, PtAg, PdAu, Au
suitable substrate 1: 96% $Al_2O_3$-Ceramic
Suitable materials for glass-ceramic for use of layer 3 are: available as commercial products Du Pont de Nemours Inc. Wilmington, DE 19898 Dielectric composition 9949, 4175
suitable crystallizing glass materials are: Dielectric composition 8299 (with restrictions)
thick-film technology, as used herein, is described for example in: Charles Harper (Ed.), Handbook of Thickfilm Hybrid Microelectronics, Chapters 5 to 7, McGraw-Hill, 1974

We claim:
1. Article of manufacture comprising
a substrate (1) comprising at least one of the materials of the group consisting of: ceramic; glass; enameled metal;
a self-supporting, free-standing membrane (3) comprising at least one of the materials of the group consisting of: glass ceramic; crystallized glass;
said membrane being formed as a solidified free-standing layer applied by thick-film technology over a filler, which has been removed, secured to the substrate and overlying a portion thereof, leaving, upon removal of the filler, a space (8) defining a chamber between the free-standing layer and the substrate,
said free-standing layer being applied over the substrate in areal form and bonded to the substrate, essentially throughout its marginal extent, leaving open a window (2a) which is small in relation to the areal extent of the free-standing layer.

2. Article according to claim 1, comprising a first electrode applied to the substrate in the region of the free space, and a second electrode (7) secured to the free-standing layer (3) at the side thereof opposite the space.

3. Article according to claim 1, comprising a first electrode (6) applied to the substrate in the region of the free space, and a second electrode (5) applied to said free-standing layer at the side thereof facing said first electrode to form, upon deformation of said layer, a contact-type switch.

4. Article according to claim 1, further comprising at least one electrical transducing element applied on the free-standing layer (3) having variable effective resistance characteristics in accordance with external parameters including at least one of: temperature; strain; compressive force; bending.

5. Article according to claim 1, wherein the thickness of the membrane is in the order of about 0.03 mm.

6. Article according to claim 1, including a tunnel-shaped duct communicating the window with said chamber, said duct having a height (H) of about 0.01 mm, and a length which is long with respect to its height.

* * * * *